US006057266A

United States Patent [19]
Colvin et al.

[11] Patent Number: 6,057,266
[45] Date of Patent: May 2, 2000

[54] MICROCLIMATE ENVIRONMENTAL CONTROL ON VEGETATION AND SEEDS EMPLOYING MICROENCAPSULATED WATER AND PHASE CHANGE MATERIALS AND METHOD

[75] Inventors: David P. Colvin, Cary, N.C.; Donald K. Cartwright, Harrison, Ark.

[73] Assignee: Delta Thermal Systems, Inc., Wake County, N.C.

[21] Appl. No.: 09/129,503

[22] Filed: Aug. 4, 1998

Related U.S. Application Data
[60] Provisional application No. 60/055,110, Aug. 6, 1997.

[51] Int. Cl.[7] .......................... A01N 25/28; A01N 25/24; A01N 63/00
[52] U.S. Cl. ........................ 504/100; 504/116; 504/117; 47/57.6; 47/DIG. 9; 47/DIG. 11
[58] Field of Search ..................... 504/117, 100, 504/116; 47/57.6, DIG. 9, DIG. 11

[56] References Cited

U.S. PATENT DOCUMENTS

| | | | |
|---|---|---|---|
| 3,157,964 | 11/1964 | Ferguson | 47/1 |
| 4,495,723 | 1/1985 | Wasserman | 47/2 |
| 4,859,377 | 8/1989 | Shasha et al. | 264/4.1 |
| 4,932,994 | 6/1990 | Koester et al. | 71/79 |
| 5,226,943 | 7/1993 | Hulshof | 71/86 |
| 5,326,573 | 7/1994 | Antfang et al. | 424/490 |
| 5,415,672 | 5/1995 | Fahey et al. | 47/57.6 |
| 5,529,772 | 6/1996 | Lebo et al. | 504/117 |
| 5,554,576 | 9/1996 | Mookerjee et al. | 504/116 |

*Primary Examiner*—S. Mark Clardy
*Attorney, Agent, or Firm*—Rosenthal & Putterman

[57] ABSTRACT

A mycoherbicide is adapted to be sprayed in solution on to an agricultural property such as seeds, germinating seeds, seedlings or plants and comprises a moisturizer such as water which is microencapsulated for time release on to the surface of agricultural property. In a further embodiment of the invention, a microencapsulated phase change material is also added to the solution to control the temperature on the surface of the agricultural property. A sticker is employed to enhance retention of the microcapsules on the agricultural property. The solution operates to control the microclimate on the surface of the agricultural property in order to enhance the effectiveness of the mycoherbicide fungi or bacteria on the host or to provide frost/freeze protection at low temperatures. In another aspect of the invention, microencapsulated phase change materials such as water and/or paraffinic hydrocarbons are applied to the surface of the agricultural property in order to regulate the microclimate to enhance germination and to limit the ability of soilborne pathogens to infect the agricultural property.

40 Claims, 2 Drawing Sheets

MICROCLIMATE ENVIRONMENTAL CONTROL ON VEGETATION AND SEEDS EMPLOYING MICROENCAPSULATED WATER AND PHASE CHANGE MATERIALS AND METHOD

PRIOR APPLICATION

This application claims priority from U.S. patent application Ser. No. 60/055,110, filed Aug. 6, 1997.

GOVERNMENT RIGHTS

This invention was developed under Small Business Innovation Research (SBIR) contract Nos. DMI 9661632 and DMI 9801183 awarded by the National Science Foundation and contract No. 98-336105908 awarded by the United States Department of Agriculture. The United States Government has certain rights in this invention.

FIELD OF THE INVENTION

This invention relates generally to the field of biological control and more particularly to natural mycoherbicides and frost/freeze/heat protection through the use of microclimate control coatings on host vegetation which are induced through the use of microencapsulated phase change materials and other microencapsulated materials.

BACKGROUND OF THE INVENTION

It is well known to employ chemical herbicides to control undesirable plant life, i.e., weeds which grow in fields of commercially grown crops (wheat, corn, soybeans and the like) as well as turf and home lawns. However, these methods have been subject to ever increasing scrutiny due to the fact that chemical herbicides have a number of drawbacks and deficiencies. While chemical herbicides have dramatically improved and increased crop productivity over the last fifty years, evidence is mounting that their misuse and overuse can have detrimental effects upon the environment. These effects include ground water contamination, human and animal health-related concerns, damage to non-target plants, and development of herbicide-resistant weed strains. These problems, coupled with increasing developmental costs, shrinking market size, and more stringent registration requirements, have prompted research into non-chemical methods of weed control for agricultural systems. One alternative method that has generated interest during the last twenty years has been the concept of mycoherbicides, a technique that uses naturally occurring fungal pathogens of specific weeds. This method involves isolating the weed's fungal pathogen(s), increasing them under artificial conditions, then applying them to their target weed in an inundative manner, in much the same way as chemical herbicides are typically applied.

Mycoherbicides have, to date, not been widely adopted because, among other things, they require relatively precise control of humidity and temperature for periods of time longer than are reliably available in nature. The present invention is therefore related to control of the fastidious microclimate environment required by mycoherbicides. When a mycoherbicide is applied to the plant surface of the target weed, the fungal spores need free moisture for an extended period to germinate, form appressoria, and penetrate the host tissues. Although variable, the periods of free moisture (in the form of dew) in the field required for successful infection and subsequent weed control is typically 12 hours or more, at a minimum. Optimum conditions would provide dew for periods extending from 24 to 48 hours. Even though a fungus can infect a weed with 12 or fewer hours of dew, typically the longer the period of free moisture, the better and more consistent the weed control. In any case, dew periods in the field fluctuate a great deal and frequently do not even meet the minimum length of time for good infection and weed control. Adequate amounts of free moisture in the field is nearly a universal requirement for all plant pathogenic fungi and is the single largest constraint to further development of many mycoherbicides. Due to the foregoing, many fungi that appeared promising under controlled conditions in the laboratory or greenhouse have been abandoned when tested in the field.

Temperature is another factor that has a marked effect on the efficacy of mycoherbicides. Plant pathogenic fungi have optimum temperature ranges for germination, appressorial development, and penetration of the host tissue. When these conditions are not met, effectiveness is reduced, eliminated, or much delayed. In particular, during the summer months, maximum daytime temperatures far exceed the range for optimum disease development, prompting the candidate fungus to slow growth, go dormant, or desiccate, all of which will reduce or eliminate the effectiveness of weed control by mycoherbicides. Further, it has been demonstrated that a constant optimum temperature is advantageous for mycoherbicides. Though many mycoherbicides have a range of temperatures under which they can be effective, that effectiveness can be greatly enhanced if a constant, optimum temperature range can be maintained on the vegetation.

Heat stress and/or sterilization of crops is another problem that cause decreases in crop yield and quality. When temperatures reach excessive levels, flower and fruit formation can be inhibited or prevented. It would therefore be of commercial value to provide a means of controlling the temperature on the surface of host vegetation to prevent heat related damage, for example, pollen sterilization due to excessive heat.

Another problem affecting crops is poor seed germination due to low soil temperatures. It would therefore be of commercial value if the germinating seed could be maintained at an optimal temperature sufficient to enable the seed to germinate and grow rapidly. In addition, a germinating seed under sub-optimal conditions is more susceptible to infection by soilborne pathogens. Furthermore, the problem of poor growth when soil temperature is below certain levels and the problem of infection by soilborne pathogens is also of concern for young plants during the early stages of plant growth. Germination of seeds and early growth of plants would be enhanced if the temperature of the seed or root environment were maintained so as to create an environment that is inhospitable to soilborne pathogens, while being more conducive for rapid seed germination.

Crop damage can occur when the temperature drops below freezing wherein all or a portion of the plant may die or flowers can be damaged to the point where they become infertile or simply fall off.

It would therefore be of significant commercial interest to provide a method of weed control in the form of a mycoherbicide which reduces or eliminates some of the deficiencies associated with the prior art.

It would also be of significant commercial interest to provide a method of improving plant growth, seed germination, flower pollination and preventing heat sterilization when the soil or the atmospheric temperatures reach extremes.

It is, therefore, an object of the present invention to provide a microenvironment for mycoherbicides which is an improvement over prior art mycoherbicides.

Another object of the present invention is to provide a mycoherbicide having enhanced effectiveness through the use of microclimate control at the surface of the host vegetation.

Another object of the present invention is to regulate the temperature and/or humidity on the surface of host vegetation through the use of microencapsulated particles in order to enhance infection and mortality of the host with a mycoherbicide.

Another object of the present invention is to provide a mycoherbicide which delivers the water molecules to the surface of the host in time release fashion in order to enhance infection of the host.

Yet another object of the present invention is to provide a mycoherbicide which is easy to apply.

A further object of the invention is to provide a mycoherbicide that is non-polluting environmentally-friendly.

A still further object of the present invention is to provide a mycoherbicide which is effective.

A still further object of the present invention is to provide a mycoherbicide which is host-specific.

A still further object of the present invention is to provide thermal regulation or microclimate control on the surface of the vegetation in order to protect the vegetation from damage due to frost and/or freeze conditions.

A still further object of the present invention is to provide thermal regulation or microclimate control on germinating seeds and early growth root systems in order to prevent infection thereof by soilborne pathogens and to provide a more conducive temperature for rapid seed germination.

A still further object of the present invention is to provide thermal regulation or microclimate control on the surface of the vegetation to protect the vegetation from damage due to high temperatures or heat stress conditions.

SUMMARY OF THE INVENTION

These and other objects are accomplished by providing an agent for enhancing the infection of host vegetation with a naturally occurring biocontrol agent, such as a bacteria or fungus. The agent comprises, in solution, a moisturizer and a sticker. The moisturizer is water or oil or other nutrients which is microencapsulated for time release on to the surface of the host. The sticker is a commercially available agricultural sticker.

In a further embodiment of the invention, a temperature control agent is microencapsulated and is applied in solution to the surface of the host to enhance mycoherbicide effectiveness.

In a further embodiment of the invention, microencapsulated water is applied in solution in time release fashion on to the surface of the host to enhance infection of the host.

In a related aspect of the invention, a temperature regulating means is applied to the surface of the plant or seed/seedling to enhance germination and growth.

In yet another aspect of the invention, microencapsulated water and/or other types of phase change materials can be applied to the plant to prevent or minimize damage from frost/freeze conditions or high temperature heat stress conditions.

BRIEF DESCRIPTION OF THE DRAWINGS

Some of the features and advantages of the invention having been briefly described, others will appear from the detailed description which follows, when taken in connection with the accompanying drawings in which.

DETAILED DESCRIPTION OF THE PREFERRED EMBODIMENTS

Figure 2A:
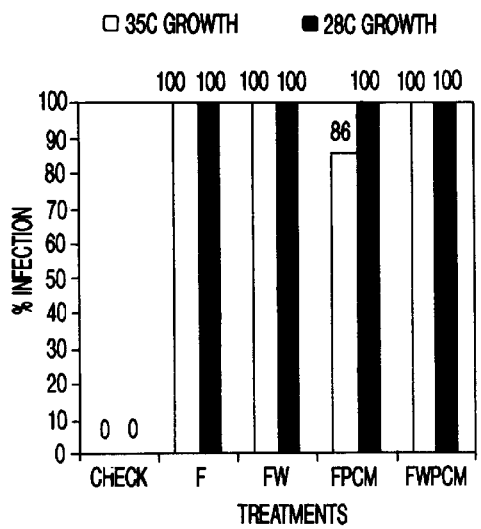
FIG. 2A illustrates the infection of pitted morningglory by *C. capsici* applied alone, in combination with microencapsulated water, in combination with a microencapsulated phase change material, or in combination with both microencapsulated water or a microencapsulated phase change material.
Figure 2B:
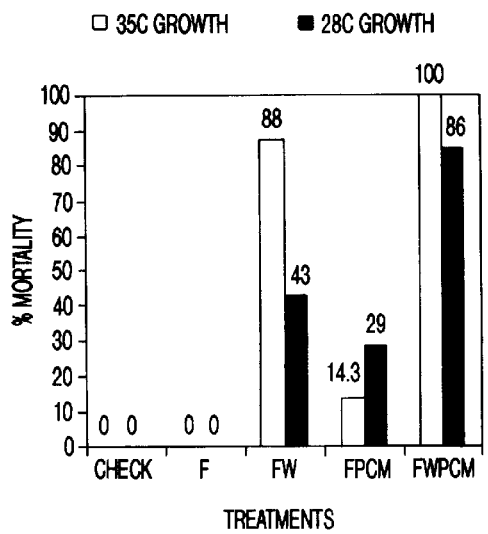
FIG. 2B illustrates the mortality of pitted morningglory by *C. capsici* applied alone, in combination with microencapsulated water, in combination with a microencapsulated phase change material, or in combination with both microencapsulated water or a microencapsulated phase change material.

While the present invention will be described more fully hereinafter with reference to the accompanying drawings, in which particular embodiments are shown, it is to be understood at the outset that persons skilled in the art may modify the invention hereindescribed while still achieving the favorable results of this invention. Accordingly, the description which follows is to be understood as a broad teaching disclosure directed to persons of skill in the appropriate art and not as limiting upon the present invention.

According to the present invention, the effectiveness of a mycoherbicide is improved through the innovative use of a solution that is sprayed on to the surface of the host vegetation or host. The solution comprises a microencapsulated moisturizing means and a means for adhering the moisturizing means to the host.

The moisturizing means takes the form of a microencapsulated moisturizing liquid such as water. Microencapsulation techniques are well-known to those skilled in the art and are in use in a wide range of industries—cosmetics and pharmaceutical. Microcapsules can be purchased from companies such as Frisby Technologies of Freeport, N.Y., Micro Tech, Inc. of Dayton, Ohio and from 3M Corporation, which is also known as Minnesota Mining and Manufacturing Corporation. In addition, there are a number of well-known texts on microencapsulation and the reader is referred to any of the following for a detailed discussion thereof:

1. Vandergaer, J. E., Ed: Microencapsulation: Processes and Applications. Plenum Press, New York, 1974.

2. Gutcho, M. H.: Microencapsules and Microencapsulation Techniques, Noyes Data Corp., Park Ridge, N.J., 1976.

3. Ranney, M. W.: Microencapsulation Technology, Noyes Development Corp., Park Ridge, N.J., 1969.

4. Kondo, A.: Microcapsule Processing and Technology. Marcel Dekker, Inc., New York 1979.

5. Nixon, J. R.: Microencapsulation. Marcel Dekker, Inc., New York, 1976.

The microcapsules as employed in the present invention have diameters ranging from about 0.50 micron to about 2000 microns. Packaged within the microcapsules is the moisturizer which in the case of the present invention is water. The water-containing microcapsules are designed for controlled time release or for no release until the core material is liberated by a specific mechanism, such as mechanical action, pressure, humidity or temperature. The microencapsulated water provides a source of moisture in addition to the natural dew period. Thus, the present invention assists in providing an environment conducive to the enhancement of the mycoherbicide by extending the length of time during which moisture is present on the host.

The solution further includes an adjuvant in the form of an agricultural sticker which assists in adhering the microcapsules to the surface of the host once the solution has evaporated or otherwise been dispersed. In addition, the solution in which the microcapsules and the sticker dispersed may be aqueous or non-aqueous. A non-aqueous solution may take the form of an oil, such as soybean oil. The application of the mycoherbicide with an invert emulsion (water surrounded by oil) is preferred in some instances over water as it prolongs the presence of moisture. The water droplets or microcapsules are surrounded by oil, which reduces the surface area of the water that is directly in contact with air and available for evaporation. It is believed that with the presence of leaky water microcapsules having the appropriate release characteristics (a function of their wall structure and permeability), the rate of evaporation of water from the surface of the leaf will be reduced, thus providing a thin film of water on the surface of the host well past the natural dew period.

In another aspect of the invention, the biocontrol agent such as a fungus or bacterium which is intended to infect the host may also be microencapsulated for time release migration on to the host according to the methods described hereinabove and added to the solution.

As discussed earlier, mycoherbicide effectiveness on the host can be further enhanced by maintaining the temperature on the surface of the host at a preselected level. According to the present invention, the temperature is controlled through the use of a microencapsulated temperature control means. The temperature control means preferably comprises a phase change material selected from the group of paraffinic hydrocarbons. The melting point of a homologous series of paraffinic hydrocarbons is directly related to the number of carbon atoms as shown in the following table:

| COMPOUND NAME | NUMBER OF CARBON ATOMS | MELTING POINT DEGREES CENTIGRADE |
| --- | --- | --- |
| n-Eicosane | 20 | 36.8 |
| n-Nonadecane | 19 | 32.1 |
| n-Octadecane | 18 | 28.2 |
| n-Heptadecane | 17 | 22.0 |
| n-Hexadecane | 16 | 18.2 |
| n-Pentadecane | 15 | 10.0 |
| n-Tetradecane | 14 | 5.9 |

The freezing point of these paraffinic hydrocarbons is normally 2–3 degrees Centigrade below the melting temperatures indicated above. When microencapsulated, these paraffinic hydrocarbons will usually exhibit an even larger difference between the melting and freezing temperatures.

In use, the appropriate solution is sprayed on to the host to be infected with the mycoherbicide. The particular formulation to be employed will depend on the host to be infected and the corresponding biological agent with which it is to be infected. Once the proper fungus and/or bacterium is selected and further in view of the anticipated weather conditions, the appropriate moisture (microencapsulated water) and temperature parameters (phase change material) are factored in to the solution to be applied to the host via conventional or electrostatic means, as the case may be.

Figure 1A:
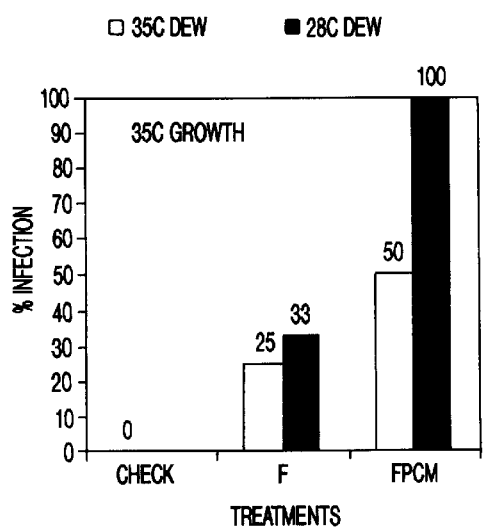
FIGS. 1A and 1B illustrates the infection rate of pitted morningglory by *C. capsici* applied alone or in combination with a microencapsulated phase change material at different dew temperatures and different growth temperatures.

The following is a laboratory example of a mycoherbicide that would be effective for infecting pitted morning glory—a common weed for soybeans. FIG. 1 shows that 24 hours of dew and temperature between 28° C. and 35° C. are most effective for control of this weed with C. capsici. In addition, FIG. 1 illustrates how a microencapsulated phase change material applied to the surface of vegetation can regulate its temperature. In a growth chamber, at either 35° C. or 28° C., microencapsulated phase change material particles significantly increased the infection rate of pitted morning glory with C. capsici.

Figure 1B:
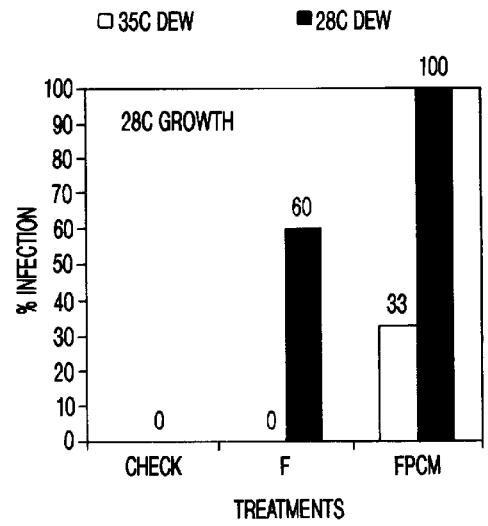

FIG. 2A illustrates how water microencapsulated for release over time (to provide moisture) in combination with microencapsulated phase change material (to provide temperature control) can provide 100% infection of the morning glory weed by C. capsici. FIG. 1B shows that the combination of these materials induces 100% mortality of this weed at the same temperatures.

In another aspect of the invention microencapsulated water is placed in solution with an appropriate sticker (or in combination with microencapsulated phase change material) and is sprayed on to the plant as described above. The water is microencapsulated for time release migration on to the plant surface and will improve the effectiveness of mycoherbicides. In another aspect of the invention, microencapsulated biological agents may be employed for disease control using conventional application methods or microencapsulated and applied as herein described. In addition, microencapsulated water and/or microencapsulated phase change material may also be used to enhance agents used for insect or pest control.

The present invention may also be employed to improve the effectiveness of many types of pesticides by maintaining the surface of the plant at a near optimum temperature for pesticide performance. Pesticides, especially herbicides (as well as fungicides and insecticides) typically have a temperature at which they operate best.

Figure 3:
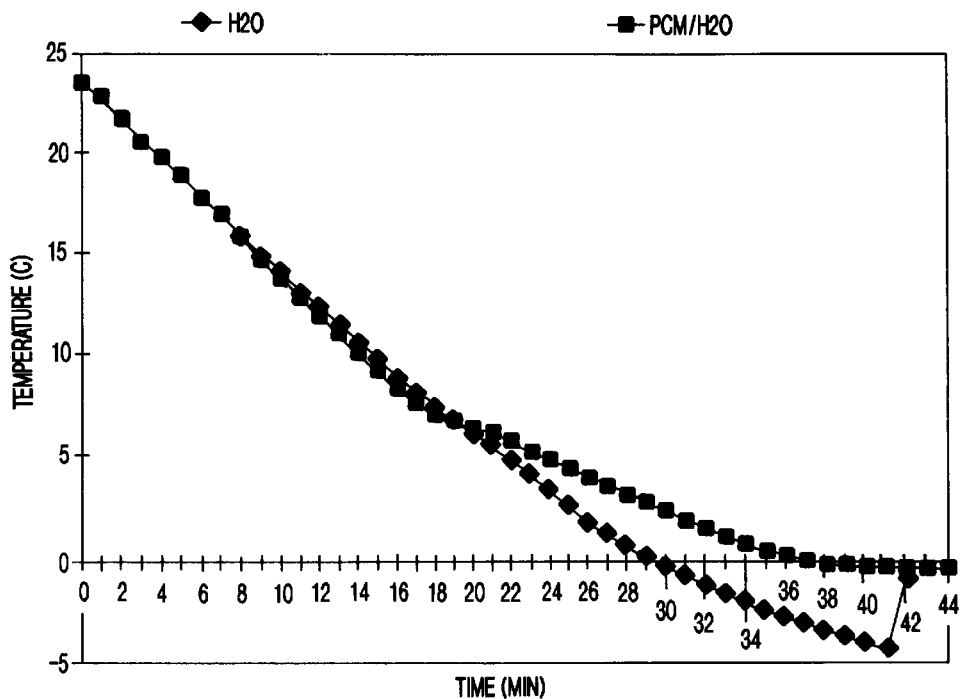
FIG. 3 illustrates the temperature inside New Guinea impatien buds when coated with PCM/water or water only solutions.
Figure 4:
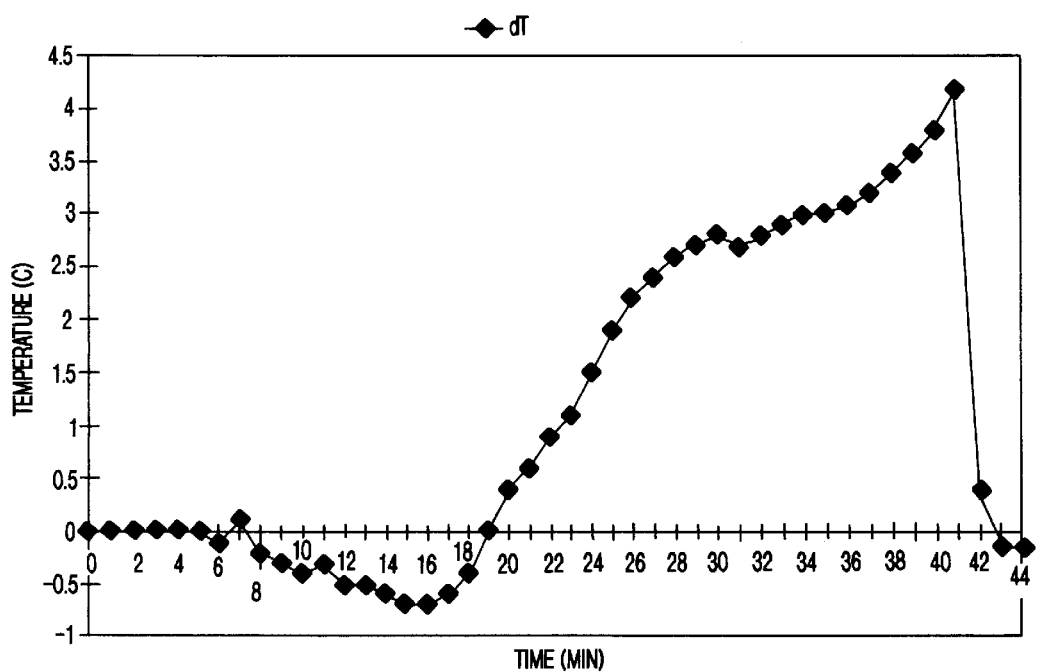
FIG. 4 illustrates the temperature difference inside New Guinea impatien buds when coated with PCM/water and water only solutions.

The present invention also has application in preventing frost/freeze damage to agricultural properties. As used herein the term agricultural property is intended to include newly planted seeds, germinating seeds, seedlings, and plants for any type of agronomic or horticulture crop. As shown in FIG. 1, the use of a coating of a microencapsulated phase change material (PCM) can provide enhanced thermal storage or protection against changes in temperature. FIG. 3 illustrates how such a PCM can store and release its latent heat in calories over a range of temperatures near 0.00 degrees Centigrade and FIG. 4 illustrates the temperature difference over time between a PCM/water mixture and a water only solution. When applied to the surface of agronomic or horticultural crops, such PCM coating would provide increased protection against freeze or frost damage.

Water may also be microencapsulated for release over time and applied to the plant as explained hereinabove. The microencapsulated water may be applied either alone or in combination with other microencapsulated phase changes material depending on the expected temperature drop. The foregoing is especially useful on fruits and vegetables as a thorough coverage of foliage and blooms with phase change materials should be effective to prevent or minimize frost/freeze damage when temperatures drop below freezing at night. In a related aspect of the invention microencapsulated phase change materials such as water and/or paraffinic hydrocarbons can be employed to mitigate against the heat stress and/or sterilization of crops. In this case, when the temperatures which might cause damage and/or sterilization are predicted, the temperature of the crops would be maintained at a lower temperature when sprayed with a solution consisting of microencapsulated water and/or other microencapsulated phase change materials, possibly in combination with a sticker, if required.

In yet another aspect of the invention microencapsulated phase change materials are employed to enhance the germination of seeds and root growth during the early stages of plant development. Currently, many crops (such as cotton) have to be replanted each year because of poor plant stands, which are primarily caused by damage to the seed or seedling just after germination, when the seedling root system development is slowed by cool temperatures or attacked by soilborne pathogens, By stabilizing the seed coat with a coating of microencapsulated agents, plant stands could be enhanced. For example, the seeds could be coated by conventional means with a microencapsulated phase change material to protect the seed from unfavorable temperature drops that would affect germination. The microencapsulated phase change material would protect the seed by slowing the rate at which the seed would cool in the event of a temperature drop, thus enhancing germination. Similarly, seeds could be protected from plant pathogens by coating them with phase change materials such that they avoid the specific temperature ranges which would be favorable for infection by plant pathogens. In accordance with the present invention, the foregoing may be microencapsulated for release over time or not, depending upon the specific application. In addition, it will be noted that a conventional sticker or other similar product may be employed in order to have the microcapsules adhere to the surface of the seed.

The foregoing embodiments and examples are to be considered illustrative, rather than restrictive of the invention, and those modifications which come within the meaning and range of equivalence of the claims are to be included therein.

That which is claimed is:

1. An agent for enhancing the effectiveness of a mycoherbicide on an agricultural property comprising in solution:
   (a) a moisturizing means microencapsulated for time release migration of moisture on to the surface of the agricultural property in an amount sufficient to control the microclimate on the surface of the agricultural property; and
   (b) means for adhering said microencapsulated moisturizing means on the surface of the agricultural property;
   whereby the microclimate on the surface of the agricultural property is controlled in order to enhance the effectiveness of a mycoherbicide thereon.

2. An agent for enhancing the effectiveness of a mycoherbicide on an agricultural property according to claim 1 wherein said moisturizing means comprises water.

3. An agent for enhancing the effectiveness of a mycoherbicide on an agricultural property according to claim 2 wherein said means for adhering comprises an agricultural sticker.

4. An agent for enhancing the effectiveness of a mycoherbicide on an agricultural property according to claim 1 further including a ph control means microencapsulated for time release migration on to the surface of the agricultural property in an amount sufficient to control the ph on the surface of the agricultural property..

5. An agent for enhancing the effectiveness of a mycoherbicide on an agricultural property according to claim 1 further including a microencapsulated temperature control means for regulating the temperature on the agricultural property and applied in an amount sufficient to regulate the temperature on the surface of the agricultural property.

6. An agent according to claim 5 wherein said microencapsulated temperature control means comprises a phase change material.

7. A biological control agent according to claim 6 wherein said phase change material is selected from the group consisting of paraffinic hydrocarbons.

8. An agent for enhancing the infection of agricultural property with a naturally occurring biocontrol agent comprising in solution:
   (a) a moisturizing means microencapsulated for time release migration of moisture on to the surface of the agricultural property in an amount sufficient to control the microclimate on the surface of the agricultural property; and
   (b) means for adhering said microencapsulated moisturizing means on the surface of the agricultural property;
   whereby the microclimate on the surface of the agricultural property is controlled in order to enhance infection of the agricultural property with the naturally occurring biocontrol agent.

9. An agent for enhancing the infection of an agricultural property with a mycoherbicide according to claim 8 further including a microencapsulated biocontrol agent in an amount sufficient to infect the agricultural property;
   whereby the preselected biocontrol agent is delivered directly to the host agricultural property.

10. An agent for enhancing the infection of an agricultural property according to claim 9 wherein said biocontrol agent is selected from the group consisting of fungi and bacteria.

11. An agent for enhancing the infection of an agricultural property with a mycoherbicide according to claim 8 further including a ph control means microencapsulated for time release migration on to the surface of the agricultural property in an amount sufficient to control the ph on the surface of the agricultural property.

12. A biocontrol agent adapted to be applied to the surface of an agricultural property comprising in solution:
   (a) a biological agent microencapsulated for time release migration on to the surface of the agricultural property in a biologically effective amount;
   (b) a moisturizing means microencapsulated for time release migration on to the surface of the agricultural property in an amount sufficient to control the microclimate on the surface of the agricultural property; and
   (c) means for adhering said microencapsulated biological agent and said microencapsulated moisturizing means to the surface of the agricultural property;
   whereby the microclimate on the surface of the agricultural property is controlled in order to enhance the infection thereof with the biological agent.

13. A biological control agent according to claim 12 wherein said solution is selected from the group consisting of aqueous and non-aqueous fluids.

14. A biological control agent according to claim 12 wherein the biological agent is host specific.

15. A biological control agent according to claim 12 wherein said biological control agent is selected from the group consisting of bacteria or fungi.

16. A biological control agent according to claim 12 wherein said moisturizing means comprises water.

17. A biological control agent according to claim 12 wherein said means for adhering comprises an agricultural sticker compound.

18. A biological control agent according to claim 12 further including a microencapsulated temperature control means for regulating the temperature on the agricultural property applied in an amount sufficient to control the temperature on the surface of the agricultural property.

19. A biological control agent according to claim 18 wherein said microencapsulated temperature control means comprises a phase change material.

20. A biological control agent according to claim 19 wherein said phase change material is selected from the group consisting of paraffinic hydrocarbons.

21. A method of infecting an agricultural property with a mycoherbicide comprising the steps of:

applying a solution containing an infectious agent and a moisturizing agent microencapsulated for time release migration of moisture on to the surface of the agricultural property in an amount sufficient to infect the agricultural property; and an agricultural sticker for adhering the moisturizing agent on the surface of the agricultural property.

22. The method of infecting an agricultural property with a mycoherbicide according to claim 21 wherein the solution further includes a microencapsulated phase change material applied in an amount sufficient to control the temperature on the surface of the agricultural property.

23. The method of infecting a host vegetation with a mycoherbicide according to claim 21 wherein the solution further includes a biocontrol agent microencapsulated applied in a biologically effective amount for time release migration of moisture on to the surface of the agricultural property.

24. A method of enhancing seed germination and early growth of a seed comprising the steps of:

coating the seed with a microencapsulated phase change material to control the microclimate on the surface of the seed;

whereby the temperature of the seed is maintained at an elevated level, thus providing enhanced frost/freeze protection and enhanced protection from soilborne pathogens.

25. The method of enhancing seed germination and early growth of a seed according to claim 24 further including the step of:

coating the seed with an agricultural sticker.

26. The method of enhancing seed germination and early growth of a seed according to claim 24 wherein the microencapsulated phase change material is selected from the group consisting of paraffinic hydrocarbons and water.

27. A method of preventing heat stress and/or sterilization of an agricultural property comprising the steps of:

applying a solution containing a microencapsulated phase change material and an agricultural sticker to the surface of the agricultural property to control the microclimate on the surface of the agricultural property;

whereby the temperature on the surface of the agricultural property is lowered, thereby enhancing crop maturation.

28. The method of preventing heat stress and/or sterilization of an agricultural property according to claim 27 wherein the microencapsulated phase change material is selected from the group consisting of paraffinic hydrocarbons and water.

29. A method of enhancing the effectiveness of an insecticide on an agricultural property, comprising the steps of:

applying a solution containing an insecticide, a microencapsulated phase change material and an agricultural sticker to the surface of the agricultural property in an insecticidally effective amount;

whereby the temperature on the agricultural property surface is maintained closer to that at which optimum insecticide performance is obtained.

30. The method according to claim 29 wherein the microencapsulated phase change material is selected from the group consisting of paraffinic hydrocarbons and water.

31. The method according to claim 29 wherein the solution further contains a preselected insecticide applied in a insecticidally effective amount.

32. A method of enhancing the effectiveness of a pesticide on an agricultural property, comprising the steps of:

applying a solution containing a pesticide in an insecticidally effective amount and a microencapsulated phase change material in an amount sufficient to control the microclimate on the surface of the agricultural property and an agricultural sticker to the surface of the agricultural property;

whereby the temperature on the surface of the agricultural property is maintained closer to that at which optimum pesticide performance is obtained.

33. The method according to claim 32 wherein the microencapsulated phase change material is selected from the group consisting of paraffinic hydrocarbons and water.

34. The method according to claim 32 wherein the solution further contains a preselected pesticide applied in an pesticidally effective amount.

35. A method of protecting an agricultural property from damage due to cold comprising the steps of:

applying to the surface of the agricultural property a solution containing a microencapsulated phase change material to control the microclimate on the surface of the agricultural property, and an agricultural sticker;

whereby the microclimate on the surface of the agricultural property is controlled in order to prevent freezing thereof.

36. The method according to claim 35 wherein the solution is a water solution.

37. The method according to claim 35 wherein the solution is an oil solution.

38. The method according to claim 35 wherein the microencapsulated phase change material is selected from the group consisting of paraffinic hydrocarbons and water.

39. The method according to claim 35 wherein the microencapsulated phase change material is water.

40. The method according to claim 35 wherein the solution contains both microencapsulated water and a microencapsulated paraffinic hydrocarbon.

* * * * *